United States Patent
Snyder

(10) Patent No.: US 6,395,027 B1
(45) Date of Patent: May 28, 2002

(54) ARTIFICIAL HEART WITH ARRHYTHMIA SIGNALLING

(75) Inventor: Alan Snyder, Hummelstown, PA (US)

(73) Assignee: The Penn State Research Foundation, University Park, PA (US)

(*) Notice: Subject to any disclaimer, the term of this patent is extended or adjusted under 35 U.S.C. 154(b) by 0 days.

(21) Appl. No.: 09/557,819

(22) Filed: Apr. 25, 2000

(51) Int. Cl.⁷ ................................................ A61M 1/12
(52) U.S. Cl. .......................... 623/3.28; 600/17; 623/3.1
(58) Field of Search ................................ 623/3.1, 3.11, 623/3.13, 3.16, 3.27, 3.28; 600/17

(56) References Cited

U.S. PATENT DOCUMENTS

| | | |
|---|---|---|
| 3,942,535 A | 3/1976 | Schulman |
| 4,143,661 A | 3/1979 | LaForge et al. |
| 4,221,543 A | 9/1980 | Cosentino et al. |
| 4,233,546 A | 11/1980 | Berthiaume |
| 4,237,895 A | 12/1980 | Johnson |
| 4,263,642 A | 4/1981 | Smmons et al. |
| 4,417,349 A | 11/1983 | Hills et al. |
| 4,439,806 A | 3/1984 | Brajder |
| 4,446,513 A | 5/1984 | Clenet |
| 4,453,537 A | 6/1984 | Spitzer |
| 4,532,932 A | 8/1985 | Batty, Jr. |
| 4,561,443 A | 12/1985 | Hogrefe et al. |
| 4,625,730 A | 12/1986 | Fountain et al. |
| 4,665,896 A | 5/1987 | LaForge et al. |
| 4,691,270 A | 9/1987 | Pruitt |
| 4,706,689 A | 11/1987 | Man |
| 4,855,888 A | 8/1989 | Henze et al. |
| 4,925,443 A | 5/1990 | Heilman et al. |
| 4,933,798 A | 6/1990 | Widmayer et al. |
| 4,941,201 A | 7/1990 | Davis |
| 4,941,652 A | 7/1990 | Nagano et al. |
| 4,947,844 A | 8/1990 | McDermott |
| 4,953,068 A | 8/1990 | Henze |
| 4,964,027 A | 10/1990 | Cook et al. |
| 4,979,506 A | 12/1990 | Silvian |
| 5,132,888 A | 7/1992 | Lo et al. |
| 5,132,889 A | 7/1992 | Hitchcock et al. |
| 5,157,593 A | 10/1992 | Jain |
| 5,279,292 A | 1/1994 | Baumann et al. |

(List continued on next page.)

FOREIGN PATENT DOCUMENTS

EP        0 412 422 A2     2/1991

OTHER PUBLICATIONS

Nazarian et al., "Development of a Totally Implantable Artificial Heart Concept to Implementation", *IEEE Case Studies in Medical Instrument Design*, pp. 95–110.

Snyder et al., "Microcomputer Control of Permanently Implanted Blood Pumps", *Computer Society Press Reprint*, pp. 154–157.

Primary Examiner—Michael J. Milano
(74) Attorney, Agent, or Firm—Marshall, Gerstein & Borun.

(57) ABSTRACT

An artificial heart assembly may be provided with a blood inlet conduit adapted to be implanted within a subject, a blood outlet conduit adapted to be implanted within the subject, a pumping mechanism implanted within the subject that pumps blood from the blood inlet conduit to the blood outlet conduit, and a motor coupled to drive the pumping mechanism. The artificial heart apparatus has a power source and a control circuit operatively coupled to cause the motor to drive the pumping mechanism in a regular mode when the power source has a relatively high charge level and in an irregular mode when the power source has a relatively low charge level so that the subject can feel when the pumping mechanism is being driven in the irregular mode and thus know that the power source has the relatively low charge level.

20 Claims, 7 Drawing Sheets

U.S. PATENT DOCUMENTS

| | | |
|---|---|---|
| 5,314,457 A | 5/1994 | Jeutter et al. |
| 5,327,335 A | 7/1994 | Maddali et al. |
| 5,345,375 A | 9/1994 | Mohan |
| 5,350,413 A | 9/1994 | Miller |
| 5,400,235 A | 3/1995 | Carroll |
| 5,438,498 A | 8/1995 | Ingemi |
| 5,444,608 A | 8/1995 | Jain et al. |
| 5,499,178 A | 3/1996 | Mohan |
| 5,515,264 A | 5/1996 | Stacey |
| 5,522,865 A | 6/1996 | Schulman et al. |
| 5,532,919 A | 7/1996 | Gegner |
| 5,559,689 A | 9/1996 | Kirchberg et al. |
| 5,569,156 A | 10/1996 | Mussivand |
| 5,569,307 A | 10/1996 | Schulman et al. |
| 5,584,870 A | 12/1996 | Single et al. |
| 5,594,635 A | 1/1997 | Gegner |
| 5,630,836 A | 5/1997 | Prem et al. |
| 5,674,281 A | 10/1997 | Snyder |
| 5,702,431 A | 12/1997 | Wang et al. |
| 5,704,891 A | 1/1998 | Mussivand |
| 5,713,939 A | 2/1998 | Nedungadi et al. |
| 5,728,154 A | 3/1998 | Crossett et al. |
| 5,741,314 A | 4/1998 | Daly et al. |
| 5,749,909 A | 5/1998 | Schroppel et al. |
| 5,751,125 A | 5/1998 | Weiss |
| 5,781,419 A | 7/1998 | Kutkut et al. |
| 5,995,874 A * | 11/1999 | Borza .......................... 623/3.1 |
| 6,149,683 A * | 11/2000 | Lancisi ....................... 623/3.1 |

\* cited by examiner

ARTIFICIAL HEART WITH ARRHYTHMIA SIGNALLING

This patent is subject to Government Contract No. NO1-HV-38130 with the National Institutes of Health.

BACKGROUND OF THE INVENTION

The present invention is directed to an arrhythmia signalling system for an artificial heart assembly.

U.S. Pat. No. 5,674,281 to Snyder discloses an artificial heart assembly having a blood inlet conduit, a blood outlet conduit, and a pumping mechanism that pumps blood from the blood inlet conduit to the blood outlet conduit. The Snyder artificial heart assembly includes a first membrane defining a blood chamber fluidly coupled to the blood inlet conduit and the blood outlet conduit, and the pumping mechanism includes a pusher plate that makes contact with the first membrane to force blood from the blood inlet conduit to the blood outlet conduit. The Snyder artificial heart assembly also has a second membrane defining a second blood chamber fluidly coupled to a second blood inlet conduit and a second blood outlet conduit and a second pusher plate. that makes contact with the second membrane to force blood from the second blood inlet conduit to the second blood outlet conduit.

U.S. Pat. No. 5,728,154 to Crossett, et al. discloses an artificial heart assembly that has a structure similar to the artificial heart assembly described above in connection with the Snyder patent. The Crosset, et al. patent also discloses a communications system that includes an external transceiver located external to Apr. 24, 2000 a subject and an internal transceiver that is implanted beneath the skin of a subject. The internal transceiver is provided with an internal coil.

U.S. Pat. No. 5,751,125 to Weiss discloses an artificial heart assembly, which is provided either as a total artificial heart or as a ventricular assist device, having a sensorless motor and a circuit for reversibly driving the sensorless motor.

U.S. Pat. No. 5,630,836 to Prem, et al. discloses a transcutaneous energy and data transmission apparatus for a cardiac assist device such as an artificial heart or ventricular assist device. The transmission apparatus has an external coupler in the form of a tuned circuit with an induction coil and an internal coupler which together act as an air-core transformer. The transmission apparatus has a DC power supply and a power converter that are coupled to the external coupler. The power converter converts electrical current from the DC power supply into high-frequency AC. The transmission apparatus has a voltage regulator coupled to the internal coupler.

SUMMARY OF THE INVENTION

In one aspect, the invention is directed to an artificial heart assembly having a blood inlet conduit adapted to be implanted within a subject, a blood outlet conduit adapted to be implanted within the subject, a pumping mechanism implanted within the subject that pumps blood from the blood inlet conduit to the blood outlet conduit, and a motor coupled to drive the pumping mechanism. The artificial heart apparatus has a power source and a control circuit operatively coupled to cause the motor to drive the pumping mechanism in a regular mode when the power source has a relatively high charge level and in an irregular mode when the power source has a relatively low charge level so that the subject can feel when the pumping mechanism is being driven in the irregular mode and thus know that the power source has the relatively low charge level.

The control circuit may cause the motor to drive the pumping mechanism in a first direction for a first time period and in a second direction for a second time period, and the control circuit may cause the pumping mechanism not to be substantially moved during a variable delay period between the first time period and the second time period, with the variable delay period having a variable duration which depends on the charge level of the power source. The variable delay period may have a relatively long duration when the power source has a relatively low charge level and a relatively short duration when the power source has a relatively high charge level.

The artificial heart apparatus may include a second power source, and the control circuit may cause the motor to drive the pumping mechanism in the irregular mode when neither of the power sources generates a voltage above a threshold voltage.

The artificial heart apparatus may also be provided with a membrane defining a blood chamber fluidly coupled to the blood inlet conduit and the blood outlet conduit, and the pumping mechanism may be provided in the form of a pusher member that makes contact with the membrane to force blood from the blood inlet conduit to the blood outlet conduit.

In another aspect, the invention is directed to an artificial heart assembly having a blood inlet conduit, a blood outlet conduit, a pumping mechanism that is adapted to pump blood from the blood inlet conduit to the blood outlet conduit, and a motor coupled to drive the pumping mechanism. The artificial heart assembly is also provided with a control circuit operatively coupled to drive the motor, the control circuit causing the motor to drive the pumping mechanism in a regular mode in response to a condition relating to the artificial heart assembly being absent and in an irregular mode in response to the condition being present so that the subject can feel when the pumping mechanism is being driven in the irregular mode and thus know that the condition is present.

The control circuit, which may include a microprocessor, a program memory, a computer program stored in the program memory, and a driver circuit, may cause the motor to drive the pumping mechanism in a first direction for a first time period and in a second direction for a second time period. The control circuit may cause the pumping mechanism not to be substantially moved during a variable delay period between the first time period and the second time, with the variable delay period having a variable duration which depends on whether the condition is present or absent. The variable delay period may have a relatively long duration when the condition is present and a relatively short duration when the condition is absent.

The invention is also directed to a method of operating an artificial heart assembly having a pumping mechanism that is adapted to pump blood from a blood inlet conduit to a blood outlet conduit. The method includes: determining whether a condition relating to the artificial heart assembly is present, if the condition relating to the artificial heart assembly is present, then driving the pumping mechanism in an irregular mode, and if the condition relating to the artificial heart assembly is not present, then driving the pumping mechanism in a regular mode.

The method may include determining whether a power source generates a voltage lower than a normal operating voltage, driving the pumping mechanism in the irregular mode if the power source generates a voltage lower than the normal operating voltage, and driving the pumping mechanism in the regular mode if the power source does not generate a voltage lower than the normal operating voltage.

The features and advantages of the present invention will be apparent to those of ordinary skill in the art in view of the detailed description of the preferred embodiment, which is made with reference to the drawings, a brief description of which is provided below.

DETAILED DESCRIPTION OF VARIOUS EMBODIMENTS

Figure 1:
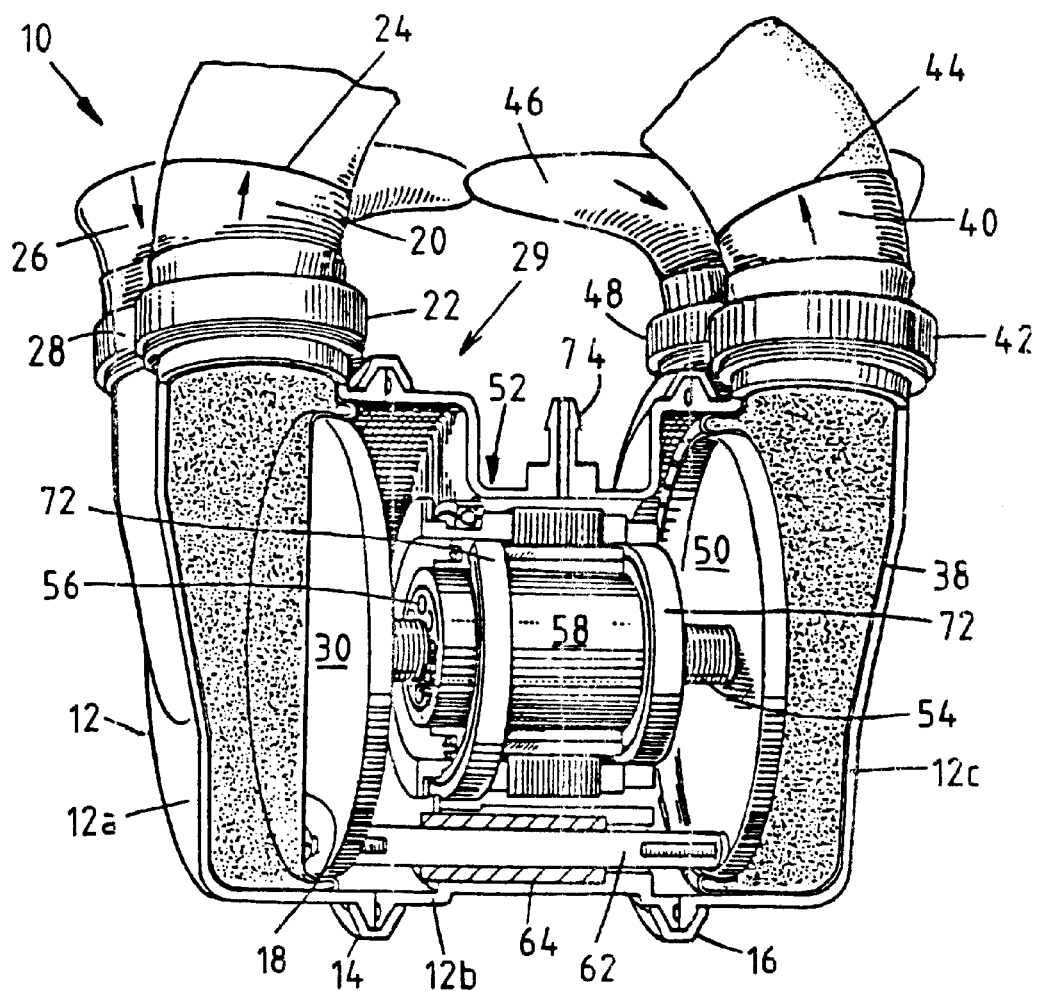
FIG. 1 is a perspective view of the mechanical portions of one possible embodiment of an artificial heart assembly, portions of which are shown in cross section.

FIG. 1 illustrates the mechanical portions of one possible embodiment of an artificial heart assembly 10 intended to be completely implanted within a subject, such as a human or an animal, to take the place of the subject's natural heart. As defined herein, an artificial heart assembly intended for use with a subject, such as an animal or human, may be a total artificial heart (TAH) intended to replace the entire heart of the subject, a ventricular assist device (VAD) intended to replace a portion of the subject's heart, or an external blood pump to be used with the subject.

The artificial heart assembly 10 has a housing 12 composed of three sections 12a, 12b, 12c which are held together by a pair of annular V-rings 14, 16. A blood reservoir within a sac 18 disposed within the housing section 12a is fluidly coupled to a blood outlet defined by an artificial vascular graft 20 connected to the housing section 12a via a threaded connector 22. The graft 20 may be connected to the pulmonary artery of the subject via a suture line 24. The blood reservoir within the sac 18 may be fluidly coupled to a blood inlet chamber defined by an artificial graft 26 which may be connected to the housing section 12a via a threaded connector 28 and to the right atrium of the subject via a suture line (not shown). A pair of one-way check valves (not shown) may be disposed in the blood inlet 26 and the blood outlet 20 to ensure that blood is pumped in the direction shown by the arrows in FIG. 1.

A blood sac 38 disposed within the housing section 12c may be fluidly coupled to a blood outlet defined by an artificial graft 40 connected to the housing section 12c via a threaded connector 42. The graft 40 may be connected to the aorta of the subject via a suture line 44. The blood reservoir in the blood sac 38 may be coupled to a blood inlet chamber defined by an artificial graft 46 which is connected to the housing section 12c via a threaded connector 48 and to the left atrium of the subject via a suture line (not shown). A pair of one-way check valves (not shown) may be disposed in the blood inlet 46 and the blood outlet 40 to ensure that blood is pumped in the direction shown by the arrows.

A pumping mechanism or pump 29 may be provided to pump blood from the blood inlet 26 to the blood outlet 20 and from the blood inlet 46 to the blood outlet 40. The pumping mechanism 29 has a pumping structure and a motor operatively coupled to drive the pumping structure. The pumping structure may be provided, for example, in the form of a pusher plate 30 that makes contact with and periodically deforms the blood sac 18 to force blood from the blood inlet 26 to the blood outlet 20 and a pusher plate 50 that makes contact with and periodically deforms the blood sac 38 to force blood from the blood inlet 46 to the blood outlet 40.

The pump 29 may include a DC brushless motor 52 that drives the pusher plates 30, 50 laterally back and forth. The motor 52 may be coupled to the pusher plates 30, 50 via a drive screw 54 and a coupling mechanism composed of a plurality of threaded elongate rollers 56 disposed within a cylindrical nut 58 fixed to a rotor (not shown) of the motor 52. Rotation of the rotor causes the nut 58 and rollers 56 to rotate, thus causing the drive screw 54 to be linearly displaced in a direction parallel to its longitudinal central axis. A guide rod 62 may be connected between the two pusher plates 30, 50 to pass through a fixed bushing 64 to prevent the plates 30, 50 from rotating. Other mechanisms for coupling the rotor to the pusher plates 30, 50 could be used.

The rotation of the rotor may be controlled via the electrical energization of a plurality of windings of a stator (not shown) which is rotatably coupled to the rotor via a pair of cylindrical bearings 72. A wire port 74 may be formed in the housing section 12b to allow the passage of wires from the windings to a controller 80 (FIG. 3), which may be implanted in another area of the subject, such as in the subject's abdomen.

The structural details of the artificial heart assembly 10 and the pumping mechanism 29 described above are exemplary only and are not considered important to the invention. Alternative designs could be utilized without departing from the invention.

Electronics

Figure 3:
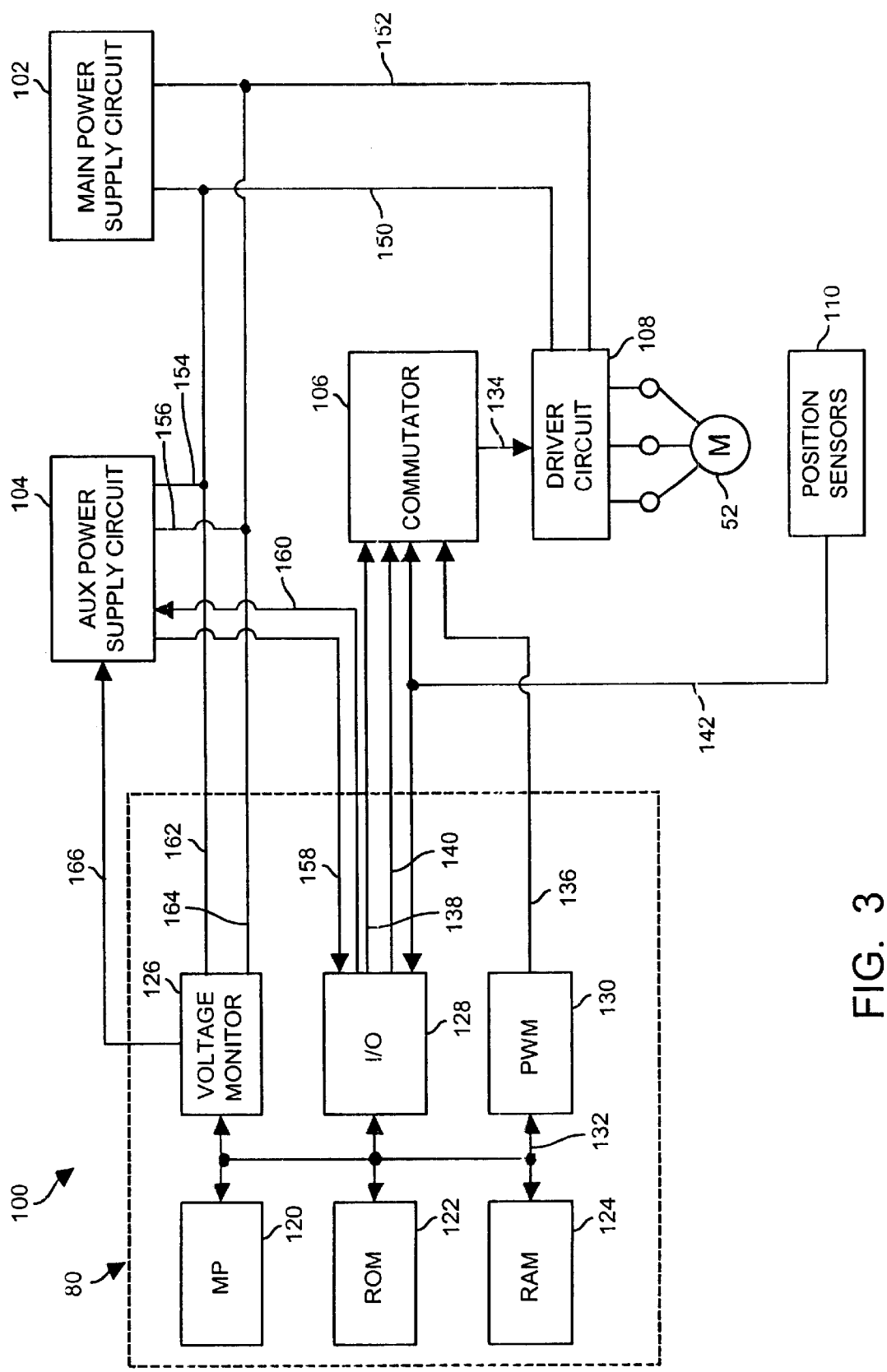
FIG. 3 is an overall block diagram of one possible embodiment of the electrical portions of an artificial heart assembly.

FIG. 3 is a block diagram of a control system 100 that may be used to control the operation of the artificial heart assembly 10. Referring to FIG. 3, the control system 100 may include the controller 80, a first power source in the form of a main power supply circuit 102, a second power source in the form of an auxiliary power supply circuit 104, a commutator 106, a driver circuit 108, the motor 52, and one or more position sensors 110.

The controller 80, which may be a conventional integrated circuit chip, may incorporate a microprocessor 120, a program memory in the form of a read-only memory (ROM) 122, a random-access memory (RAM) 124, a voltage monitoring circuit 126, an input/output (I/O) circuit 128, and a pulse-width modulator (PWM) circuit 130, all of which are interconnected via an address/data bus 132.

The commutator circuit 106 periodically generates a set of commutation signals which are transmitted to the driver circuit 108 via a multi-line conductor 134. The driver circuit 108 generates a set of electrical drive signals that are transmitted to the stator windings of the motor 52 via three lines connected to three terminals of the motor 52.

The commutator 106 may be provided with a PWM signal from the PWM circuit 130 via a conductor 136, a direction signal that specifies the direction in which the motor 52 should be driven from the I/O circuit 128 via a conductor 138, and a brake signal which indicates when an electronic "brake" should be applied from the I/O circuit 128 via a conductor 140. The position sensors 110, which may be Hall-effect sensors for example, generate a set of position signals that are indicative of the angular position of the rotor of the motor 52 with respect to the stator. The position signals are transmitted to the I/O circuit 128 and to the commutator 106 via a conductor 142.

During operation, the commutator 106 periodically generates a set of commutation signals and transmits them to the driver circuit 108 to drive the motor 52. The commutation signals may be generated in a conventional manner based upon a three-bit position signal generated by the position sensors 110 and based upon a PWM signal generated by the PWM circuit 130. Alternatively, sensorless positioning could be utilized, such as that disclosed in U.S. Pat. No. 5,751,125 to Weiss, which is incorporated by reference herein.

The duty cycle or pulse width of the PWM signal may be used to control the amount of acceleration of the motor 52, with a relatively large duty cycle corresponding to a relatively high rate of acceleration and a relatively small duty cycle corresponding to a relatively low rate of acceleration.

Further details regarding how the controller 80 could be used to operate the motor 52 are disclosed in U.S. Pat. No. 5,751,125 to Weiss and U.S. Pat. No. 5,674,281 to Snyder, both of which are incorporated herein by reference.

Still referring to FIG. 3, the main power supply circuit 102 supplies electric power to the motor 52 through the driver circuit 108 via a pair of power lines 150, 152. The main power supply circuit 102, which acts as a power source, could include an externally located battery, an externally located DC-to-AC converter connected to provide power to an internal coil disposed beneath the skin of a subject via an external coil, and an AC-to-DC converter coupled to the internal coil, as disclosed in each of the following patent applications, for which William Weiss is the named inventor and which are incorporated by reference herein: U.S. Ser. No. 09/557,813 filed Apr. 25, 2000 and entitled "Artificial Heart Power Supply System"; U.S. Ser. No. 09/557,814 filed Apr. 25, 2000 and entitled "Artificial Heart With Synchronous Rectification"; U.S. Ser. No. 09/557,809 filed Apr. 25, 2000 and entitled "Artificial Heart Data Communication System"; U.S. Ser. No. 09/557,811 filed Apr. 25, 2000 and entitled "Artificial Heart With Energy Recovery"; and U.S. Ser. No. 09/557,810 filed Apr. 25, 2000 and entitled "Artificial Heart With Metal Detection."

The auxiliary power supply circuit 104, which may include a rechargeable battery disposed within the subject, may supply electric power to the power lines 150, 152 via a pair of power lines 154, 156. The auxiliary power supply circuit 104 may generate and provide a sensing signal to the I/O circuit 128 via a sensing line 158, and a control signal may be transmitted to the auxiliary power supply circuit 104 via a control line 160.

The voltage monitoring circuit circuit 126 may be connected to sense the voltage across the power lines 150, 152 via a pair of lines 162, 164 and may provide a control signal to the auxiliary power supply circuit 104 via a line 166 based on the sensed voltage.

Figure 2:
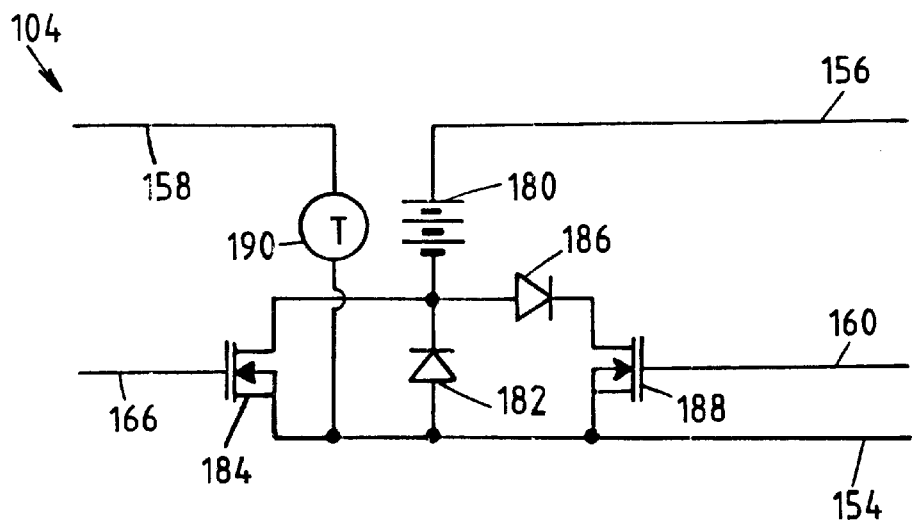
FIG. 2 is a circuit diagram of one embodiment of an auxiliary power supply circuit shown schematically in FIG. 3.

One possible embodiment of the auxiliary power supply circuit 104 is shown in FIG. 2. Referring to FIG. 2, the auxiliary power supply circuit 104 may. be provided with a rechargeable battery 180 disposed within the subject and a diode 182. Assume that the power lines 152 and 156 represent positive power lines and that the power lines 150, 154 represent negative power lines (e.g. grounded lines). In that case, due to the interconnection of the positive power lines 152, 156 and the interconnection of the negative power lines 150, 154, when the supply voltage across the positive power lines 152, 156 becomes less than the voltage provided by the battery 180, the diode 182 will become conductive and electric power will be provided by the battery 180 via the power lines 154, 156.

A switching transistor 184 may be provided in parallel with the diode 182 and may be switched on to effectively short out the diode 182 when the battery 180 is supplying electric power. The voltage monitoring circuit 126 may be used to sense the voltage across the lines 162, 164 to determine when the battery 180 is supplying electrical power (e.g. when the voltage across the lines 162, 164 falls below a predetermined voltage) and to cause the transistor 184 to turn on, via the control line 166, to short out the diode 182. When the transistor 184 is turned on, the supply of power is more efficient since the transistor 184 has a lower impedance than the diode 182.

The auxiliary power supply circuit 104 may be provided with a charging circuit in the form of a diode 186 and a switching transistor 188. The charging circuit may be turned on occasionally to recharge the battery 180 with electric power provided by the main power supply circuit 102. To recharge the battery 180, the transistor 188 is turned on via a control signal provided by the I/O circuit 128 via the line 160. When the transistor 188 is turned on, electric current flows from the power line 152 connected to the main power supply circuit 102, to the power line 156, to the battery 180, and through the diode 186 and the turned-on transistor 188.

The charging circuit may be occasionally or periodically activated as necessary to keep the battery 180 fully charged. For example, the controller 80 could keep track of the amount of time that the battery 180 is supplying electric current (e.g. by keeping track of the amount of time that the voltage across the lines 162, 164 is below a threshold voltage), and the controller 80 could cause the battery 180 to be recharged after a predetermined amount of usage.

The auxiliary power supply circuit 104 may also be provided with a temperature sensor 190 disposed adjacent the battery 180 to determine when the battery 180 is being used, or has been used for a predetermined amount of time. The recharging of the battery 180 could be controlled or affected by the sensing signal generated by the temperature sensor 190 on the line 158. For example, recharging could be disabled if the battery 180 is supplying power instead of the main power supply circuit 102.

Pumping Modes

Figure 4A:
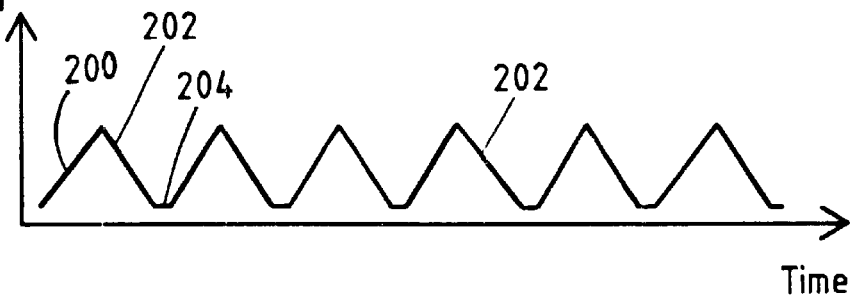
FIGS. 4A and 4B illustrate various manners in which an artificial heart assembly in accordance with the invention may be operated.
Figure 4B:
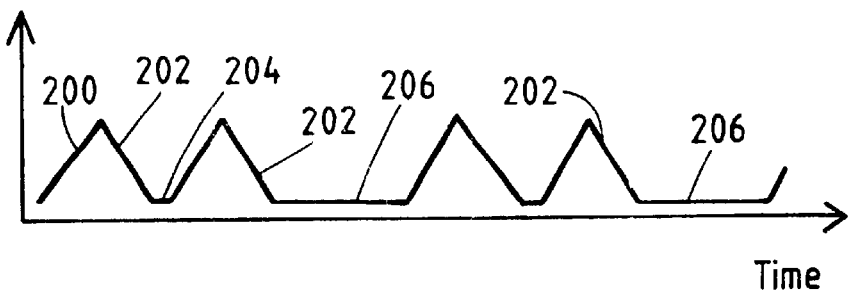

FIGS. 4A and 4B illustrate two ways in which a pumping mechanism incorporated in the artificial heart assembly 10, such as the pusher plate 30, may be reciprocably driven. The following description is made with reference to the pusher plate 30, e.g. the pusher plate 30 is referenced in the determination of whether the artificial heart assembly 10 is in systole, diastole, or diastasis. Alternatively, the pusher plate 50 could be used as the reference pusher plate. Furthermore, where the artificial heart assembly 10 is in the form of a ventricular assist device, there would be only one pusher member that could be used as a reference. Where two pusher plates or pumping mechanisms are utilized, they could be driven independently.

Referring to FIG. 4A, the pusher plate 30 may be driven in one direction for a period of time, as indicated by a positive-slope segment 200, which is referred to herein as the "systolic direction." In general, the term "systole" may be defined as referring to "a recurrent contraction of the heart during which blood is pumped out of a cavity of the heart." Thus, the pusher plate 30 is driven in the systolic direction when it compresses its blood reservoir, i.e. when the pusher plate 30 moves to the left in FIG. 1.

Subsequently, the pusher plate 30 may be driven in an opposite direction for a period of time, as indicated by a negative-slope segment 202, which is referred to herein as the "diastolic direction." In general, the term "diastole" may be defined as referring to "a recurrent expansion of the heart during which a cavity of the heart is filled with blood." Thus, the pusher plate 30 is driven in the diastolic direction when it moves away from its associated blood reservoir, i.e. when the pusher plate 30 moves to the right in FIG. 1.

Following the end of each movement in the diastolic direction, there is a relatively brief period of time, as indicated by a horizontal segment 204, during which there is no significant pusher plate movement. That time period is referred to as "diastasis" or "asystole." The diastasis time period may be 20 milliseconds, for example, or a period of greater or lesser duration.

The pusher plate motion shown in FIG. 4A is a regular motion in that each cycle of the pusher plate 30 is identical or substantially identical, e.g. the duration and slope of the segments 200 in each cycle are substantially identical, the duration and slope of the segments 202 in each cycle are substantially identical, and the duration of the segments 204 in each cycle are substantially identical.

FIG. 4B illustrates a different manner in which the pusher plate 30 may be driven. Referring to FIG. 4B, the pusher plate 30 is driven in the same systolic and diastolic directions, as represented by the segments 200, 202. However, the delay or time period following the end of each movement in the diastolic direction is a variable time period instead of a constant time period. In particular, some of the diastolic movements are followed by a relatively short time period or delay, represented by the segments 204, during which there is no significant movement of the pusher plate 30, and other diastolic movements are followed by a relatively long time period or delay, represented by the segments 206, during which there is no significant movement of the pusher plate 30.

The delays 204, 206 are preferably different enough so that the subject in which the artificial heart assembly 10 is implanted can physically feel the difference between the pusher plate motion shown in FIG. 4A and the pusher plate motion shown in FIG. 4B. Consequently, the operation of the artificial heart assembly 10 can be changed from that shown in FIG. 4A to that shown in FIG. 4B in order to "send" the subject a message, such as a low battery signal or an abnormal operating condition signal.

When operating as shown in FIG. 4B, the artificial heart assembly 10 may be said to be in "arrhythmia," which may be defined as "an alteration of the rhythm of the heartbeat either in time or force." Instead of varying the duration of the delays 204, 206, other changes could be made to operate the artificial heart assembly 10 in arrhythmic mode, such as by significantly altering the speed of movement of the plate 30, so as to change the pumping force it exerts to a sufficient degree so that the subject can detect the change.

Battery Check Routine

The overall operation of the artificial heart assembly 10 may be controlled by one or more computer programs stored in the program memory 122 and executed by the microprocessor 120. For example, a status check routine may be utilized to periodically check the operational status of the artificial heart assembly 10, its internal electronics, or its power source(s).

Figure 5:
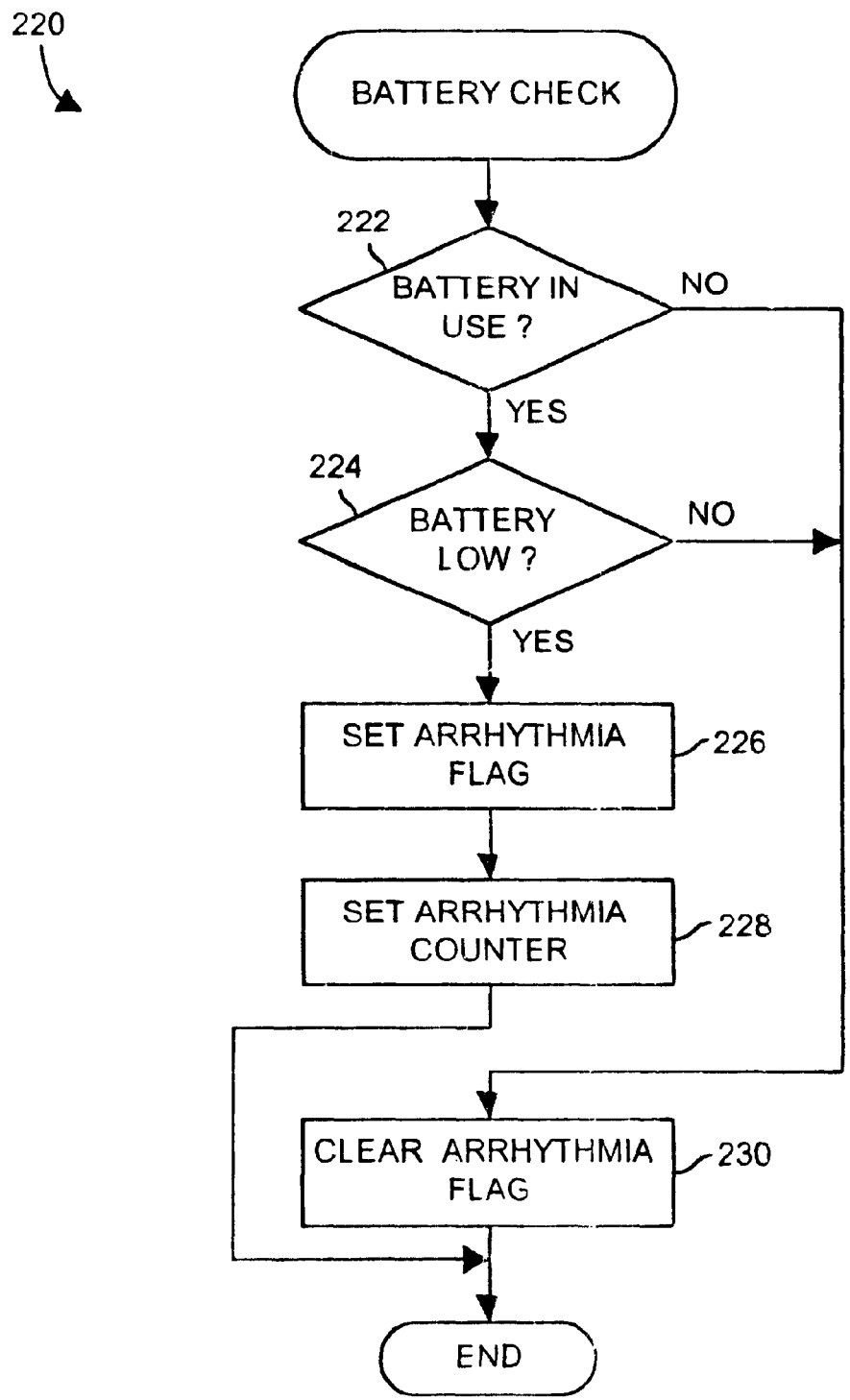
FIG. 5 is a flowchart of a battery check routine that may be utilized in an artificial heart assembly.

One example of such a status check routine is shown in FIG. 5 as a battery check routine 220. The battery check routine 220 may be periodically performed, such as once a minute or once every 10 minutes, to determine if the power provided by one of the power sources 102, 104 is less than desired, which could be accomplished in various ways, such as by comparing the voltage output on the power lines 150, 152 with a threshold voltage.

Referring to FIG. 5, block 222 may be performed to determine whether the battery 180 (FIG. 2) is in use. Whether the battery 180 is in use may be determined, for example, by comparing the voltage being supplied on the lines 162, 164 (FIG. 3) with a threshold voltage. For example, assume that the lowest voltage supplied by the main power supply circuit 102 is 13.8 volts and that the battery 180 (FIG. 2) supplies 13 volts. If the voltage across the lines 162, 164 is less than 13.8 volts, it can be assumed that the battery 180 is being used.

If the battery 180 is being used as determined at block 222, the routine may branch to block 224 where the battery 180 (and/or another power source) is checked to determine whether it is low. If a low power condition is detected at block 224, the routine branches to block 226 where an arrhythmia flag, which will cause the artificial heart assembly 10 to operate in the mode shown in FIG. 4B (or in another arrhythmic mode), is set.

A low battery condition could be considered to exist, for example, by the battery voltage falling below a threshold, such as 10 volts in the above example. Alternatively, a low battery condition could be determined by the amount of time the battery 180 was used. As another alternative, a low battery condition could be assumed to exist based on a combination of the time that the battery was being used and the magnitude of the current that was drawn from the battery.

After block 226, in the case of a low power condition, block 228 may be performed to set an arrhythmia counter (not shown) to specify how often the longer delay periods 206 (FIG. 4B) are to be utilized. For example, if the arrhythmia counter is set to two at block 228, every other cycle will have a relatively long delay period 206, as shown in FIG. 4B. If the arrhythmia counter is set to three at block 228, every third cycle will have a relatively long delay period 206.

If no low power condition is detected at block 224, the routine branches to block 230 where the arrhythmia flag is cleared to indicate such state.

Direction Routine

Figure 6:
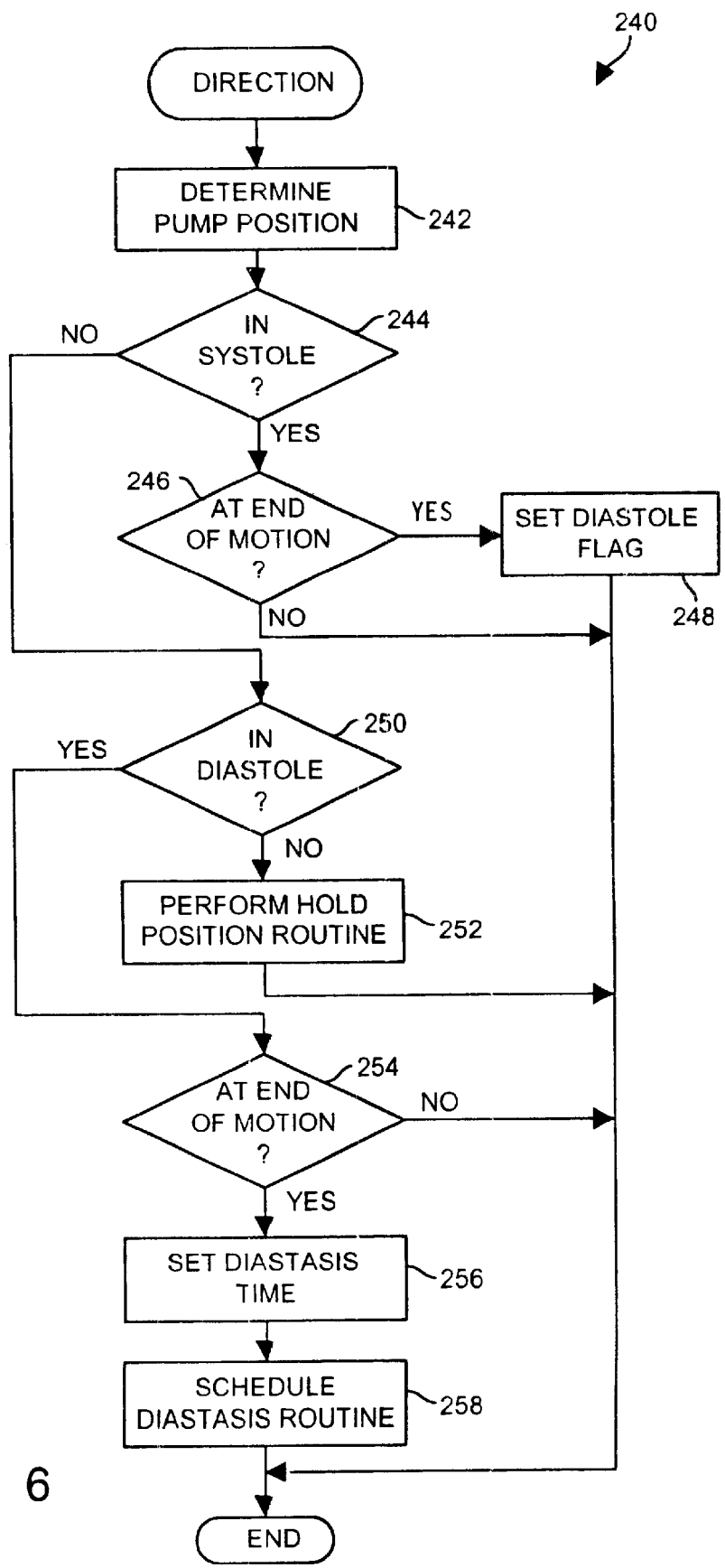
FIG. 6 is a flowchart of a direction routine that may be utilized in an artificial heart assembly.

The operation of the artificial heart assembly 10 may be controlled utilizing a direction routine 240 shown in FIG. 6. The basic purpose of the direction routine 240 is to track the direction or state, i.e. systolic, diastolic, diastasic, of the artificial heart assembly 10. The direction routine 240 may be performed once each time the pusher plate 30 incrementally changes position, which can be determined by the position sensors 110 or in a sensorless manner as described in U.S. Pat. No. 5,751,125 to Weiss, which is incorporated by reference herein.

Referring to FIG. 6, at block 242 the current position of the pusher plate 30 is determined. The current position of the pusher plate 30 could be kept track of in software. For example, assume that 1,000 successive sets of commutation signals are required the move the pusher plate 30 from its fully retracted position (which corresponds to the start of each rising segment 200 shown in FIG. 4B) to its fully extended position (which corresponds to the end of each rising segment 200 shown in FIG. 4B). In that case, the position of the pusher plate 30 could be assigned a position number that varies between 1 and 1,000, with the current position number specifying the absolute position of the pusher plate 30. As the pusher plate 30 is reciprocably driven, the current position number could be incremented or decremented, depending on the current direction in which the pusher plate 30 is being driven.

At block 244, the routine determines whether the artificial heart assembly 10 is in systole, e.g. whether the pusher plate 30 is moving leftward as represented by the segment 200 in FIGS. 4A and 4B. If so, the routine branches to block 246 where it determines whether the pusher plate 30 is at the end of its systolic motion. Where the possible position of the pusher plate 30 ranges from 1 to 1,000, as described above, the determination made at block 246 could be made by comparing the current position of the pusher plate 30 with 1,000.

If the pusher plate 30 is at the end of its motion as determined at block 246, the routine branches to block 248 wherein a diastole flag is set to indicate that the direction of motor 52 which is driving the pusher plate 30 needs to be changed (as described above, the line 138 from the I/O circuit 128 to the commutator 106 specifies the motor direction).

If the artificial heart assembly 10 is not in systole as determined at block 244, the routine branches to block 250 where it determines whether the artificial heart assembly 10 is in diastole. This may be determined by checking the motor direction specified by the direction line 138. If the artificial heart assembly 10 is not in diastole as determined at block 250, then it is assumed that the artificial heart assembly 10 is in the delay or diastasis state represented by one of the segments 204 or 206 shown in FIGS. 4A and/or 4B. In that case, the routine branches to block 252 where a hold position routine 252 may be performed to keep the motor 52, and thus the pusher plate 30, stationary or substantially stationary.

If the artificial heart assembly 10 is in diastole as determined at block 250, the routine branches to block 254 wherein it determines whether the pusher plate 30 is at the end of its motion. If it is, which means that the diastasis or delay period 204 or 206 should commence, then a diastasis time is set at block 256 and a diastasis routine 260 (FIG. 7). is scheduled at block 258.

The diastasis time set at block 256 may be the relatively small time period represented by the segments 204. The diastasis routine 260 may be scheduled at block 258 to be performed a predetermined period of time in the future, such as four milliseconds in the future.

Diastasis Routine

Figure 7:
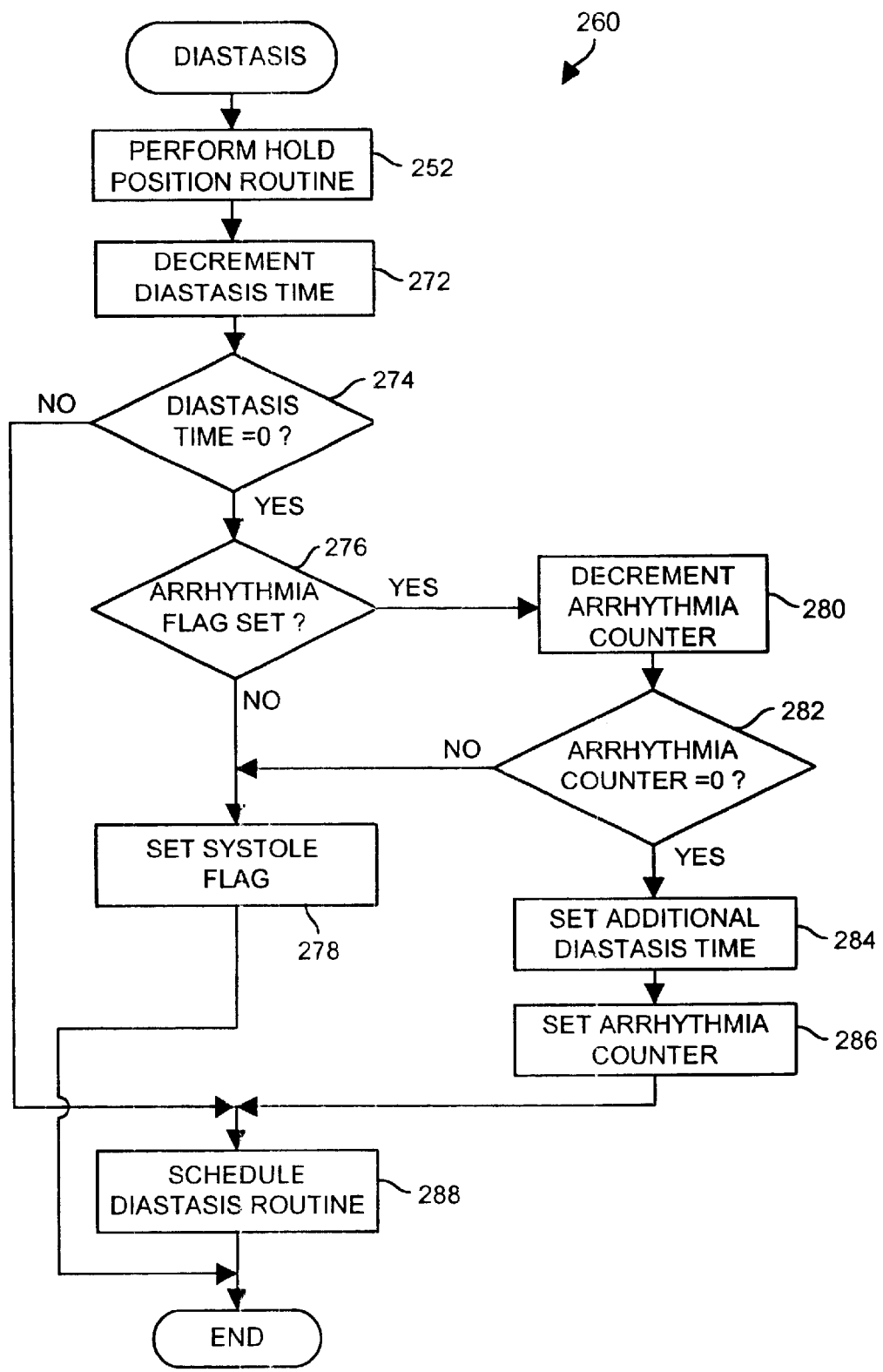
FIG. 7 is a flowchart of a diastasis routine that may be utilized in an artificial heart assembly.

The diastasis routine 260 shown in FIG. 7 may be used to control the duration of the diastasis mode to be either a relatively short-duration delay period 204 or a relatively long-duration delay period 206 and to control how often the relatively long-duration delay periods 206 are utilized.

Referring to FIG. 7, at block 252 the hold position routine may be performed. At block 272, the diastasis time is decremented. The diastasis time may be tracked as a count of a counter (hardware or software), with each count corresponding to a predetermined period of time, such as four milliseconds. At block 274, if the diastasis time (or count) is not zero, meaning that additional time is required to complete the delay 204 or 206, then the routine branches to block 288 where the diastasis routine 260 is again scheduled to be performed a predetermined period of time, such as four milliseconds, in the future.

If the diastasis time is zero as determined at block 274, meaning that the pusher plate 30 has been stationary or substantially stationary for a time period corresponding to the segments 204, the routine branches to block 276 where it determines whether the arrhythmia flag is set (which means that the longer delay periods 206 should be utilized).

If the arrhythmia flag is not set as determined at block 276, meaning that the pusher plate 30 should be driven in the systolic direction since the requisite delay period 204 has elapsed, then the routine branches to block 278 where a systole flag is set (which causes the direction signal on the direction line 138 to specify the systolic direction).

If the arrhythmia flag is set as determined at block 276, meaning that an additional delay period should be utilized, then the routine branches to block 280 where the arrhythmia counter (that is described above and that was set at block 228 of FIG. 5) is decremented by one.

At block 282, if the arrhythmia counter is not equal to zero, then the current delay period should be a relatively short-duration period 204 (as noted above and shown in FIG. 4B, when a low battery condition is detected, not all delay periods are short-duration periods 204), in which case the routine branches to block 278 where the systole flag is set.

If the arrhythmia counter is equal to zero as determined at block 282, then the current delay period should be a relatively long-duration period 206, and the routine branches to block 284 where an additional diastasis time is added to cause a longer delay period 206. The routine then branches to block 286 where the arrhythmia counter is set to its original value, e.g. two or three, so that a long-duration delay period 206 is not inserted again until the desired cycle.

Hold Position Routine

Figure 8:
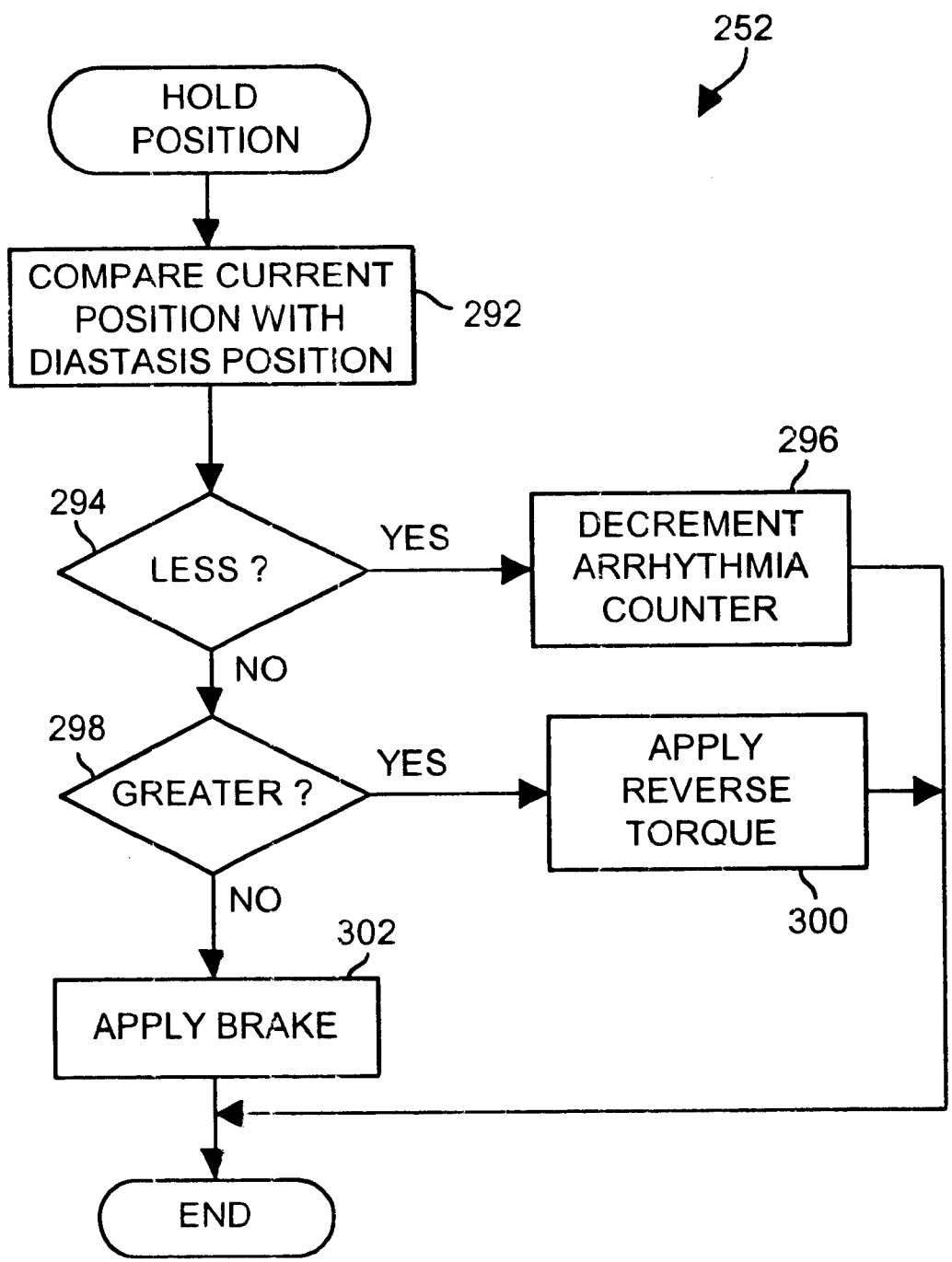
FIG. 8 is a flowchart of a hold position routine that may be utilized in an artificial heart assembly.

FIG. 8 is a flow chart of one embodiment of the hold position block 252 shown schematically in FIGS. 6 and 7. The general purpose of the hold position routine 252 is to attempt to hold the pusher plate 30 at a fixed position. Referring to FIG. 8, at block 292 the current position of the pusher plate 30 may be compared with a predetermined diastasis position. For example, if the pusher plate 30 can occupy a range of positions between 1 and 1,000, the predetermined diastasis position could be position 1.

At block 294, if the current position is less than the desired diastasis position, the routine branches to block 296 where a forward torque is applied to move the plate 30 to its desired diastasis position. At block 298, if the current position is greater than the desired diastasis position, the routine branches to block 300 where a reverse torque is applied to move the plate 30 to its desired diastasis position. At block 302 an electronic brake, such as that disclosed in U.S. Pat. No. 5,674,281 to Snyder which is incorporated by reference herein, may be applied.

The actions described above in connection with the flowchart shown in FIG. 8 are not necessary in the practice of the invention, and the artificial heart assembly 10 may be operated substantially differently than the manner described above in connection with the flowcharts shown in FIGS. 5–7.

Numerous additional modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. An artificial heart assembly, comprising:
   a blood inlet conduit adapted to be implanted within a subject;
   a blood outlet conduit adapted to be implanted within the subject;
   a pumping mechanism adapted to be implanted within the subject that pumps blood from said blood inlet conduit to said blood outlet conduit;
   a motor coupled to drive said pumping mechanism;
   a power source; and
   a control circuit operatively coupled to cause said motor to drive said pumping mechanism in a regular mode when said power source has a relatively high charge level, said control circuit causing said motor to drive said pumping mechanism in an irregular mode when said power source has a relatively low charge level so that the subject can feel when said pumping mechanism is being driven in said irregular mode and thus know that said power source has said relatively low charge level.

2. An artificial heart assembly as defined in claim 1 wherein said control circuit causes said motor to drive said pumping mechanism in said irregular mode when said power source generates a voltage below a threshold voltage.

3. An artificial heart assembly as defined in claim 1 additionally comprising a second power source, wherein said control circuit causes said motor to drive said pumping mechanism in said irregular mode when neither of said power sources generates a voltage above a threshold voltage.

4. An artificial heart assembly as defined in claim 1 wherein said control circuit causes said motor to drive said pumping mechanism in a first direction for a first time period, wherein said control circuit causes said motor to drive said pumping mechanism in a second direction for a second time period, and wherein said control circuit causes said pumping mechanism not to be subtantially moved during a variable delay period between said first time period and said second time period, said variable delay period having a variable duration which depends on said charge level of said power source.

5. An artificial heart assembly as defined in claim 1 wherein said control circuit causes said motor to drive said pumping mechanism in a first direction for a first time period, wherein said control circuit causes said motor to drive said pumping mechanism in a second direction for a second time period, and wherein said control circuit causes said pumping mechanism not to be subtantially moved during a variable delay period between said first time period and said second time period, said variable delay period having a relatively long duration when said power source has said relatively low charge level and said variable delay period having a relatively short duration when said power source has said relatively high charge level.

6. An artificial heart assembly as defined in claim 1 additionally comprising a membrane defining a blood chamber fluidly coupled to said blood inlet conduit and said blood outlet conduit, wherein said pumping mechanism comprises a pusher member which makes contact with said membrane to force blood from said blood inlet conduit to said blood outlet conduit.

7. An artificial heart assembly as defined in claim 1 additionally comprising:
   a first membrane defining a blood chamber fluidly coupled to said blood inlet conduit and said blood outlet conduit, wherein said pumping mechanism comprises a pusher member which makes contact with said first membrane to force blood from said blood inlet conduit to said blood outlet conduit;
   a second membrane defining a second blood chamber fluidly coupled to a second blood inlet conduit and a second blood outlet conduit; and
   a second pusher member which makes contact with said second membrane to force blood from said second blood inlet conduit to said second blood outlet conduit.

8. An artificial heart assembly comprising:
   a blood inlet conduit;
   a blood outlet conduit;
   a pumping mechanism that is adapted to pump blood from said blood inlet conduit to said blood outlet conduit;
   a motor coupled to drive said pumping mechanism; and
   a control circuit operatively coupled to drive said motor, said control circuit comprising a microprocessor, a program memory, a computer program stored in said program memory, and a driver circuit, said control circuit causing said motor to drive said pumping mechanism in a regular mode in response to a condition relating to said artificial heart assembly being absent, said control circuit causing said motor to drive said pumping mechanism in an irregular mode in response to said condition being present so that a subject can feel when said pumping mechanism is being driven in said irregular mode and thus know that said condition is present.

9. An artificial heart assembly as defined in claim 8 additionally comprising a power source, wherein said control circuit causes said motor to drive said pumping mechanism in said irregular mode when said power source generates a voltage below a threshold voltage.

10. An artificial heart assembly as defined in claim 9 additionally comprising a second power source, wherein said control circuit causes said motor to drive said pumping mechanism in said irregular mode when neither of said power sources generates a voltage above a threshold voltage.

11. An artificial heart assembly as defined in claim 8 wherein said control circuit causes said motor to drive said pumping mechanism in a first direction for a first time period, wherein said control circuit causes said motor to drive said pumping mechanism in a second direction for a second time period, and wherein said control circuit causes said pumping mechanism not to be subtantially moved during a variable delay period between said first time period and said second time period, said variable delay period having a variable duration which depends on whether said condition is present or absent.

12. An artificial heart assembly as defined in claim 8 wherein said control circuit causes said motor to drive said pumping mechanism in a first direction for a first time period, wherein said control circuit causes said motor to drive said pumping mechanism in a second direction for a second time period, and wherein said control circuit causes said pumping mechanism not to be subtantially moved during a variable delay period between said first time period and said second time period, said variable delay period having a relatively long duration when said condition is present and said variable delay period having a relatively short duration when said condition is absent.

13. An artificial heart assembly as defined in claim 8 additionally comprising a power source, wherein said control circuit causes said motor to drive said pumping mechanism in a first direction for a first time period, wherein said control circuit causes said motor to drive said pumping mechanism in a second direction for a second time period, and wherein said control circuit causes said pumping mechanism not to be subtantially moved during a variable delay period between said first time period and said second time period, said variable delay period having a variable duration which depends on whether said power source generates a relatively high voltage or a relatively low voltage.

14. An artificial heart assembly as defined in claim 8 additionally comprising a power source, wherein said control circuit causes said motor to drive said pumping mechanism in a first direction for a first time period, wherein said control circuit causes said motor to drive said pumping mechanism in a second direction for a second time period, and wherein said control circuit causes said pumping mechanism not to be subtantially moved during a variable delay period between said first time period and said second time period, said variable delay period having a relatively long duration when said power source generates a relatively low voltage and said variable delay period having a relatively short duration when said power source generates a relatively high voltage.

15. A method of operating an artificial heart assembly having a pumping mechanism that is adapted to pump blood from a blood inlet conduit to a blood outlet conduit, said method comprising:
   determining whether a condition relating to the artificial heart assembly is present;
   if said condition relating to the artificial heart assembly is present, then driving the pumping mechanism in an irregular mode; and
   if said condition relating to the artificial heart assembly is not present, then driving the pumping mechanism in a regular mode.

16. A method as defined in claim 15 comprising:
   determining whether a power source generates a voltage lower than a normal operating voltage;
   driving the pumping mechanism in said irregular mode if the power source generates a voltage lower than said normal operating voltage; and
   driving the pumping mechanism in said regular mode if the power source does not generate a voltage lower than said normal operating voltage.

17. A method as defined in claim 15 comprising:
   driving the pumping mechanism in a first direction for a first time period;
   driving the pumping mechanism in a second direction for a second time period; and
   waiting a variable delay period between said first time period and said second time period in which the pumping mechanism is not substantially moved, said variable delay period having a variable duration which depends on whether said condition is present or absent.

18. A method as defined in claim 15 comprising:
   driving the pumping mechanism in a first direction for a first time period;
   driving the pumping mechanism in a second direction for a second time period;
   waiting a relatively long delay period between said first time period and said second time period in which the pumping mechanism is not substantially moved;
   driving the pumping mechanism in a first direction for a first time period;
   driving the pumping mechanism in a second direction for a second time period; and
   waiting a relatively short delay period between said first time period and said second time period in which the pumping mechanism is not substantially moved.

19. A method as defined in claim 15 wherein the artificial heart assembly includes a power source, said method comprising:
   determining if the power source generates a voltage lower than a normal operating voltage;
   driving the pumping mechanism in a first direction for a first time period;
   driving the pumping mechanism in a second direction for a second time period; and
   waiting a variable delay period between said first time period and said second time period in which the pumping mechanism is not substantially moved, said variable delay period having a variable duration which depends on whether the power source generates a voltage lower than said normal operating voltage.

20. A method as defined in claim 15 wherein the artificial heart assembly includes a power source, said method comprising:
   determining if the power source generates a voltage lower than a normal operating voltage;
   driving the pumping mechanism in a first direction for a first time period;
   driving the pumping mechanism in a second direction for a second time period;
   waiting a relatively long delay period between said first time period and said second time period in which the pumping mechanism is not substantially moved;
   driving the pumping mechanism in a first direction for a first time period;
   driving the pumping mechanism in a second direction for a second time period; and
   waiting a relatively short delay period between said first time period and said second time period in which the pumping mechanism is not substantially moved.

* * * * *

UNITED STATES PATENT AND TRADEMARK OFFICE
CERTIFICATE OF CORRECTION

PATENT NO. : 6,395,027 B1  
DATED : May 28, 2002  
INVENTOR(S) : Alan J. Snyder

It is certified that error appears in the above-identified patent and that said Letters Patent is hereby corrected as shown below:

<u>Drawings,</u>
Figure 8, Step 296, please delete "DECREMENT ARRHYTHMIA COUNTER" and insert -- APPLY FORWARD TORQUE -- therefor.

Signed and Sealed this

Twenty-ninth Day of October, 2002

*Attest:*

JAMES E. ROGAN
*Attesting Officer*           *Director of the United States Patent and Trademark Office*

UNITED STATES PATENT AND TRADEMARK OFFICE
CERTIFICATE OF CORRECTION

PATENT NO. : 6,395,027 B1
DATED : May 28, 2002
INVENTOR(S) : Alan J. Snyder

It is certified that error appears in the above-identified patent and that said Letters Patent is hereby corrected as shown below:

Title page,
Item [56], U.S. PATENT DOCUMENTS, "5,749,909 A" please delete "Schroppel" and insert -- Schroeppel -- therefore.

Column 1,
Line 29, please delete "Crosset" and insert -- Crossett -- therefore.
Line 31, please delete "Apr. 24, 2000".

Column 2,
Line 47, please delete "second time" and insert -- second time period -- therefore.

Column 5,
Line 63, please delete "circuit circuit 126" and insert -- circuit 126 -- therefore.

Column 6,
Line 60, please delete "reciprocably" and insert -- reciprocally -- therefore.

Column 8,
Line 63, please delete "diastasic" and insert -- diastatic -- therefore.

Column 9,
Line 15, please delete "reciprocably" and insert -- reciprocally -- therefore.

Column 11,
Line 50, please delete "subtantially" an insert -- substantially -- therefore.

Column 12,
Line 58, please delete "subtantially" an insert -- substantially -- therefore.

UNITED STATES PATENT AND TRADEMARK OFFICE
CERTIFICATE OF CORRECTION

PATENT NO. : 6,395,027 B1
DATED : May 28, 2002
INVENTOR(S) : Alan J. Snyder

It is certified that error appears in the above-identified patent and that said Letters Patent is hereby corrected as shown below:

Column 13,
Lines 2, 15 and 27, please delete "subtantially" an insert -- substantially -- therefore.

Signed and Sealed this

Fifteenth Day of July, 2003

JAMES E. ROGAN
*Director of the United States Patent and Trademark Office*